US00PP24833P3

(12) United States Plant Patent
Slaybaugh

(10) Patent No.: US PP24,833 P3
(45) Date of Patent: Sep. 2, 2014

(54) APPLE TREE NAMED 'DAS-10'

(50) Latin Name: *Malus domestica*
Varietal Denomination: DAS-10

(71) Applicant: DAS 10, LLC, Biglerville, PA (US)

(72) Inventor: David A. Slaybaugh, Biglerville, PA (US)

(73) Assignee: DAS 10, LLC, Biglerville, PA (US)

( * ) Notice: Subject to any disclaimer, the term of this patent is extended or adjusted under 35 U.S.C. 154(b) by 166 days.

(21) Appl. No.: 13/573,597

(22) Filed: Sep. 27, 2012

(65) Prior Publication Data

US 2013/0086713 P1 Apr. 4, 2013

Related U.S. Application Data

(60) Provisional application No. 61/626,521, filed on Sep. 29, 2011.

(51) Int. Cl.
*A01H 5/00* (2006.01)
*A01H 5/08* (2006.01)

(52) U.S. Cl.
CPC ..... *A01H 5/0875* (2013.01)
USPC ..... Plt./161

(58) Field of Classification Search
USPC ..... Plt./161
See application file for complete search history.

*Primary Examiner* — Wendy C Haas
(74) *Attorney, Agent, or Firm* — James A. Lucas; Driggs, Hogg, Daugherty & Del Zoppo Co., LPA

(57) ABSTRACT

A new and distinct strain of apple, designated 'DAS-10', originated as a whole tree mutation in a 'Honeycrisp' planting. The fruit ripen 21 days earlier than parent tree fruit, which will provide fruit producers with an opportunity to sell high quality apple fruit earlier than either 'Honeycrisp' or 'Gala.' Fruit color and eating quality are similar to 'Honeycrisp.'

4 Drawing Sheets

Latin name of genus and species: *Malus domestica.*
Variety name: 'DAS-10'.

BACKGROUND OF THE DISCLOSURE

This invention relates to apple trees and, more specifically, to an apple tree referred to as a strain, or bud mutation, of *Malus domestica* Borkh. 'Honeycrisp' (U.S. Plant Pat. No. 7,197).

I discovered this new and unique strain of apple tree as a whole tree mutation in a cultivated area near Biglerville, Pa. The tree of this invention produces a fruit of attractive commercial value, with a significantly earlier ripening date than the parent (U.S. Plant Pat. No. 7,197). Fruit maturity is 21 days earlier than 'Honeycrisp'; however new strain fruit quality and color characteristics are similar to those of the parent. Based on starch index tests, optimum harvest in 2010 for 'DAS-10' began on August 11 and for 'Honeycrisp' began on September 1. In 2011 optimum harvest for 'DAS-10' began on August 12 and for 'Honeycrisp' began on September 2. In 2012, starch index tests again confirmed that fruit maturity is 21 days earlier than for 'Honeycrisp'.

This new strain of apple tree was asexually reproduced by top grafting in Biglerville, Pa. and bud grafting near Aspers, Pa., and grafting has shown this new strain to come true in two successive generations. This propagation of the new strain by grafting under standard controlled conditions discloses the continued maintenance of the characteristics described herein which distinguish this new strain from the parent cultivar.

SUMMARY OF THE INVENTION

This new and distinctive strain of apple tree produces a fruit that matures 21 days earlier than 'Honeycrisp' and 'Gala'.

Fruit internal quality is exceptional, being similar to the parent. Fruit skin color and appearance also are similar to 'Honeycrisp.'

DESCRIPTION OF THE DRAWINGS

This new strain of apple tree is illustrated by the accompanying photographic drawings, depicting the plant by the best possible color representation using color photography.

BOTANICAL DESCRIPTION OF THE PLANT

Figure 1:
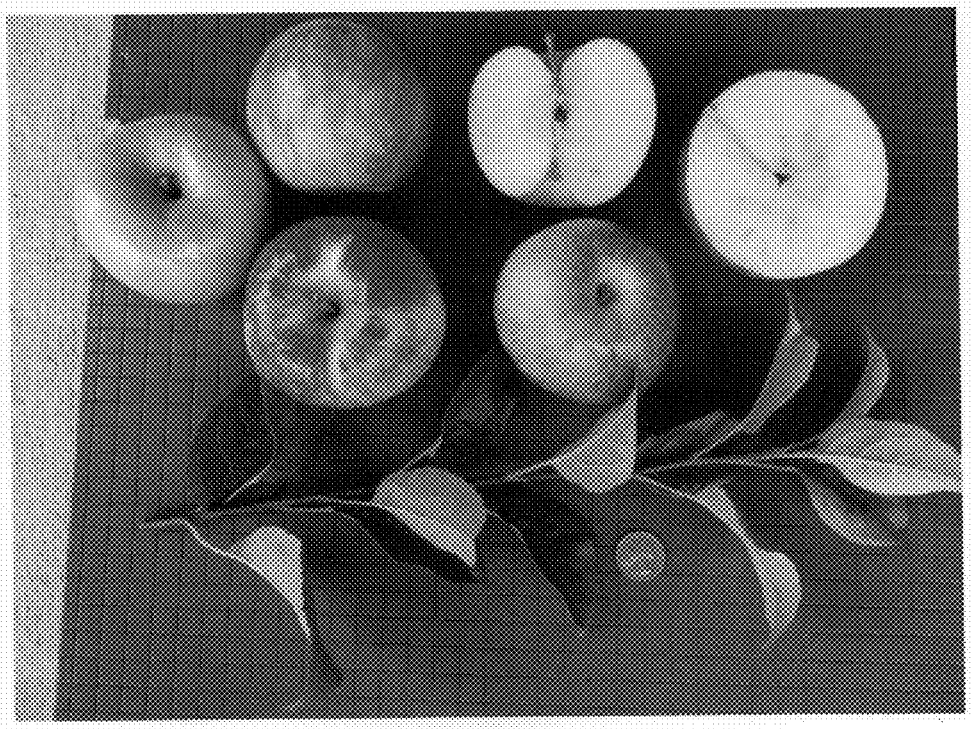
FIG. 1: Green apple on left is 'Honeycrisp' parent harvested on Aug. 11, 2010. Remaining fruit and leaves are 'DAS-10' harvested on Aug. 11, 2010—optimum harvest date based on starch index tests. At top, three whole fruit specimens in different orientations showing stem cavity, calyx and general shape and color and two partially dissected fruit showing flesh and seed cavity; at bottom, a terminal shoot showing current season's growth, leaves, leaf arrangement and leaf spacing.
Figure 2:
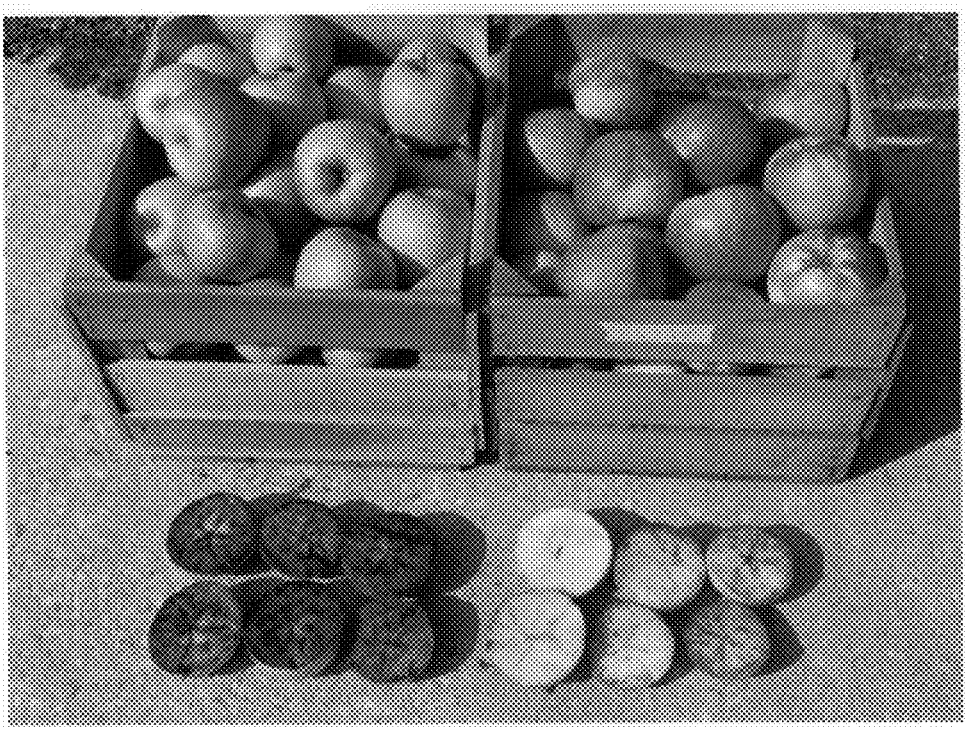
FIG. 2: Top: On left, crate of 'Honeycrisp' harvested on Aug. 11, 2010, compared to, on right, crate of new strain, harvested on the same date, representing characteristic background and blush color development. Bottom: Starch index test comparisons, on the same date, of 'Honeycrisp,' on left, and 'DAS-10,' on the right. Dark staining indicates that starches have not yet converted to sugars.
Figure 3:
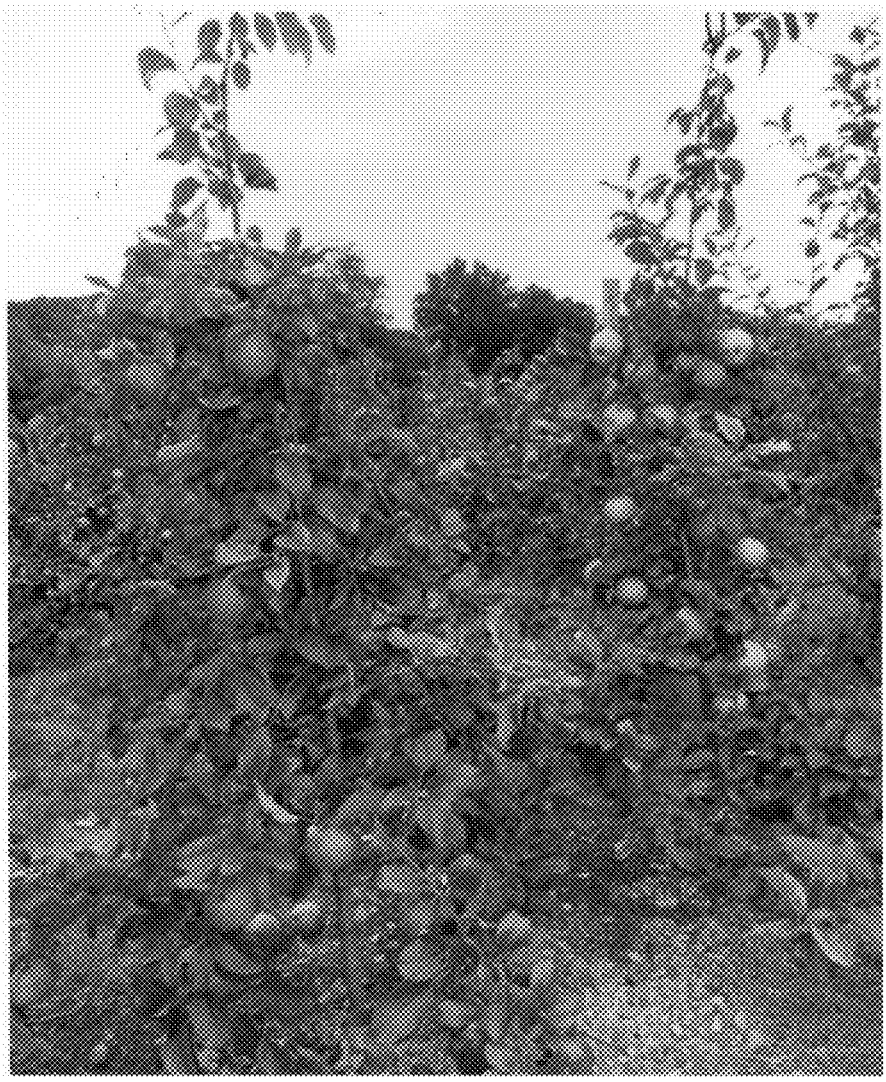
FIG. 3: 'DAS-10' tree, on left, compared to 'Honeycrisp' tree, on right.
Figure 4:
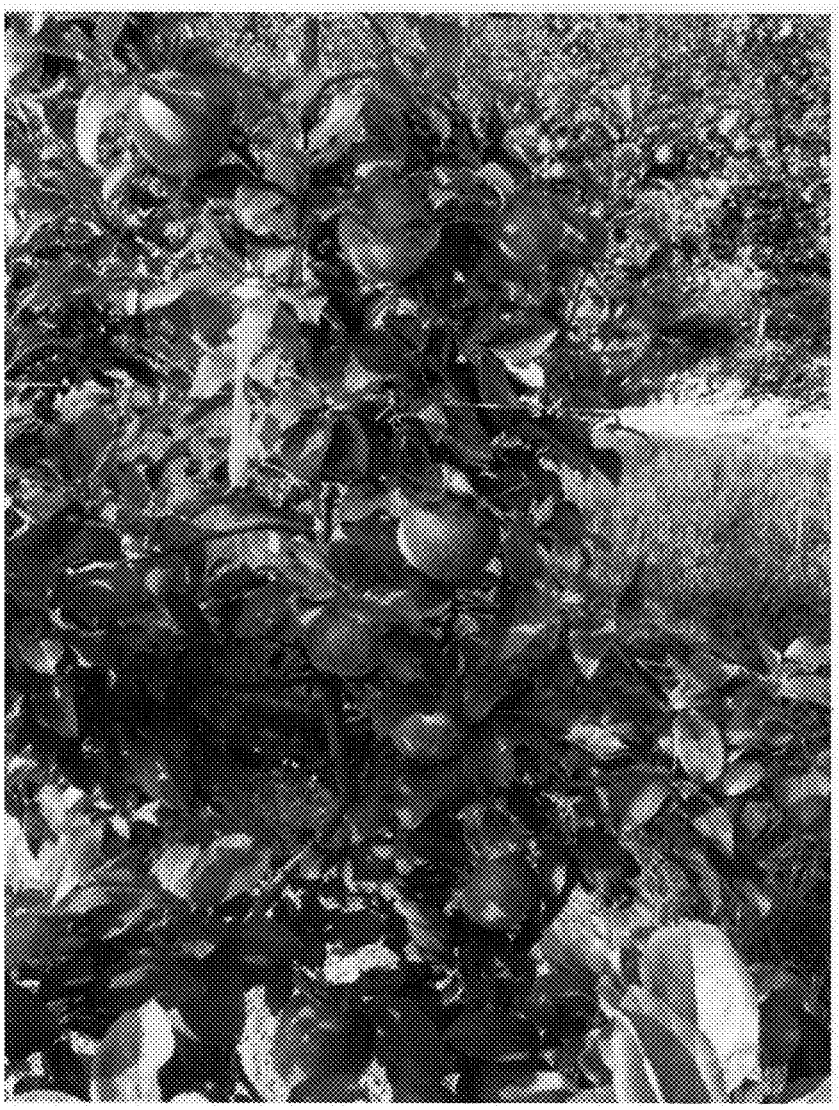
FIG. 4: Branch, bark, leaf and fruit characteristics of 'DAS-10.' Note mottling on leaves, a characteristic unique to 'Honeycrisp.'

All color references below are measured against *The Royal Horticultural Society Colour Chart*. Colors are approximate as color depends on horticultural practices such as light level and fertilization rate, among others.

Parentage: Whole tree mutation in a planting of 'Honeycrisp' trees. Asexually reproduced by top-working and also bud grafting.

Tree: 2.5 m tall by 1.6 m wide and 8.4 kg fruit per tree, on Malling 9 at 5 years age, near Biglerville, Pa. Upright-spreading tree of medium vigor, hardy, productive, annual bearer.

*Trunk.*—Diameter 4.6 cm at 20 cm height above soil level, moderately smooth, gray, R.H.S. (Royal Horticultural Society) 201A.

Branches:

*Thickness.*—14.4 mm, average branching, 70-80 degree crotch angles, gray-orange, RHS 165A.

*Lenticels.*—Approximately 16 per $cm^2$, slightly raised, 2.5 mm long.

*Terminal shoots.*—Average length 25 cm, gray-orange, 165B.

Leaves:

*Length.*—7.2 cm.

*Width.*—5.0 cm. Semi-glossy, mostly flat, non-undulating, ovate with acuminate apex and rounded base, medium thick, dark green, RHS 137B for upper foliage surface, RHS 138B for lower surface, some having chlorotic margins and blotching.

*Venation.*—Reticulate pattern, green, RHS 138B.

*Margins.*—More broadly serrated than 'Honeycrisp' (3.7 vs 2.4 mm apart).

*Petioles.*—Length 2.4 cm, diameter 2 mm at mid-section, green, RHS 138B, some red at base.

*Stipules.*—0 to 2, length 8.2 mm, green, RHS 137B.

Flowers:

*Dates of first and full blossoms.*—April 27 and May 1 in Biglerville, Pa. in 2011; April 10 and 15, 2012. Mid-season bloom period.

*Color.*—White, RHS 155D.

*Corolla diameter.*—3.0 cm.

*Pedicel length.*—2.5 cm.

*Flower petals.*—Shape ovate, texture soft.

Fruit:

*Maturity when described.*—Firm-ripe.

*Date of first harvest.*—Aug. 12, 2011, mean starch level of 5.57, compared to 1.14 for 'Honeycrisp' harvested from same location (Cornell University 8 point scale, with 1 being immature and 8 being over-mature, Blanpied and Silsby, 1992).

*Date of second harvest.*—Aug. 16, 2011, mean starch level of 5.71, compared to 1.14 for 'Honeycrisp' harvested from same location (Cornell University scale).

*Uniformity of maturity.*—Requires two harvests, four days apart, similar to 'Honeycrisp.'

*Size.*—Uniformly large.

*Diameter.*—8.0 to 8.5 cm.

*Form.*—Mostly oblate, some conic, regular cross-section.

*Cavity.*—Flaring, depth 10 mm, breadth 15 by 17 mm, gold-russet markings.

*Stem.*—Gold, RHS 22A, some brown, RHS 177A, lightly pubescent, length 13 mm, diameter 2.5 mm, 0 bracts.

*Basin.*—Depth 13 mm, breadth 17 mm.

*Calyx.*—Mostly closed, sepals persistent with erect tips, diameter 4.8 mm.

*Skin.*—Medium thick, glossy, medium cuticle wax.

*Lenticels.*—Small to medium size, moderate number, circular, white, RHS 155B, scattered over most of surface, more numerous near basin.

*Russet.*—Slight, mainly around cavity, gold, RHS 163B.

*Ground color.*—Yellow-green, RHS 1D.

*Color markings.*—Red blush, over 40 to 60% of surface, bright scarlet red, RHS 58B, some blotches.

*Bloom.*—Scant.

*Scarfskin.*—Occasional.

*General color effect.*—Scarlet red over yellow-green background with gold stem cavity.

*Flesh.*—Juicy, cream color, RHS 159D.

*Texture.*—Firm, medium grained, crisp.

*Flavor.*—Delicious tart/sweet blend.

*Aroma.*—Mildly aromatic.

*Eating quality.*—Exceptional, 13 to 14% soluble solids, 16 to 17 lbs firmness at harvest maturity.

Core: Equidistant between calyx and stem ends.

*Carpellary area.*—Visible.

*Depth of calyx tube.*—10 mm.

*Seed cells.*—Axile, closed, 5 in number.

*Cell walls.*—Thin, obovate to lanceolate in longitudinal section, narrow in cross-section (length 5.8 mm, breadth 3 mm), surface non-tufted.

Seeds: Usually 10, length 7 mm, breadth 3 mm, form acute.

*Color.*—Brown, RHS 166A.

Uses: Excellent for fresh wholesale and retail markets.

Keeping quality: Similar to 'Honeycrisp' in same planting.

Resistance to insects: Similar to 'Honeycrisp'.

Resistance to diseases: Similar to 'Honeycisp'.

Other observations: Very winter hardy, moderate tolerance to drought and heat, moderate susceptibility to storage disorders (similar to parent).

I claim:

1. A new and distinct strain of apple tree, as illustrated and described, characterized by significantly earlier fruit maturity than the high quality cultivar, 'Honeycrisp.' Fruit quality is equal to that of 'Honeycrisp'.

* * * * *